(12) United States Patent
Fix et al.

(10) Patent No.: US 9,513,250 B2
(45) Date of Patent: Dec. 6, 2016

(54) MICROELECTROCHEMICAL SENSOR AND METHOD FOR OPERATING A MICROELECTROCHEMICAL SENSOR

(71) Applicant: Robert Bosch GmbH, Stuttgart (DE)

(72) Inventors: Richard Fix, Gerlingen (DE); Andreas Krauss, Tuebingen (DE); Kathy Sahner, Leonberg (DE); Denis Kunz, Untergruppenbach (DE); Philipp Nolte, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 351 days.

(21) Appl. No.: 14/217,550

(22) Filed: Mar. 18, 2014

(65) Prior Publication Data

US 2014/0262834 A1 Sep. 18, 2014

(30) Foreign Application Priority Data

Mar. 18, 2013 (DE) .......................... 10 2013 204 665

(51) Int. Cl.
*G01N 27/406* (2006.01)
*G01N 27/409* (2006.01)
*G01N 27/12* (2006.01)

(52) U.S. Cl.
CPC ........ *G01N 27/4067* (2013.01); *G01N 27/123* (2013.01); *G01N 27/128* (2013.01); *G01N 27/409* (2013.01)

(58) Field of Classification Search
CPC .. G01N 27/406; G01N 27/409; G01N 27/123; G01N 27/128
See application file for complete search history.

(56) References Cited

U.S. PATENT DOCUMENTS

2004/0075140 A1\* 4/2004 Baltes .................... G01N 27/12
257/347

FOREIGN PATENT DOCUMENTS

DE 199 41 051 A1 3/2001
DE 10 2012 201 304 A1 8/2013

\* cited by examiner

*Primary Examiner* — Jennifer Dieterle
(74) *Attorney, Agent, or Firm* — Maginot, Moore & Beck LLP

(57) ABSTRACT

A microelectrochemical sensor includes a carrier material composed of a semiconductor substrate, and includes a chemosensitive sensor element. The chemosensitive sensor element is positioned in a first partial region of the carrier material. A heating element is positioned in a region of the chemosensitive sensor element and is configured to regulate a temperature of the chemosensitive sensor element. A microelectronic unit is positioned in a second partial region of the carrier material, and is connected to the chemosensitive sensor element and the heating element via conductor tracks integrated into the carrier material. The microelectronic unit is configured to operate the heating element and the sensor element.

10 Claims, 2 Drawing Sheets

MICROELECTROCHEMICAL SENSOR AND METHOD FOR OPERATING A MICROELECTROCHEMICAL SENSOR

This application claims priority under 35 U.S.C. §119 to patent application no. DE 10 2013 204 665.0, filed on Mar. 18, 2013 in Germany, the disclosure of which is incorporated herein by reference in its entirety.

BACKGROUND

The present disclosure relates to a microelectrochemical sensor and to a method for operating a microelectrochemical sensor from a sensor bus.

In order to be able to adapt a ratio between a quantity of fuel for a combustion process and an available quantity of oxygen, a statement about an oxygen concentration in an exhaust gas of the combustion process is required. Since the exhaust gas at a measuring location is usually at a high temperature, a temperature-resistant sensor is required for determining the oxygen concentration.

DE 199 41 051 A1 describes a sensor element for determining the oxygen concentration in gas mixtures and a method for producing the same.

SUMMARY

Against this background, the present disclosure presents a microelectrochemical sensor and a method for operating a microelectrochemical sensor from a sensor bus. Advantageous configurations are evident from the claims and the following description.

As a result of the miniaturization of sensor components of a sensor, an electronic unit of the sensor can be arranged in direct proximity to the sensor components. As a result, a construction of the sensor can be simplified. Moreover, it is possible to implement a connection of the sensor to a network of sensors without interposed electronics for operating the sensor. Miniaturization of a sensor element of the sensor makes it possible to reduce a required heating power for regulating the temperature of the sensor element. As a result, enough electrical energy for operating the sensor can be obtained for example from a sensor interface provided for data transfer.

A microelectrochemical sensor comprises the following features:
a carrier material composed of a semiconductor substrate or composed of a material which can be structured with the aid of a semiconductor process;
a chemosensitive sensor element, which is arranged in a first partial region of the carrier material;
a heating element, which is arranged in the region of the sensor element and is designed to regulate the temperature of the sensor element; and
a microelectronic unit, which is arranged in a second partial region of the carrier material, wherein the microelectronic unit is connected to the sensor element and the heating element via conductor tracks integrated into the carrier material, wherein the microelectronic unit is designed to operate the heating element and the sensor element.

A microelectrochemical sensor can be understood to be a miniaturized chemosensitive sensor which can provide an electrical signal as measurement variable. The sensor can comprise at least one sensor element.

In accordance with one embodiment, the sensor element can be a ceramic membrane which is conductive for ions of a specific chemical species and is fashioned on both sides as ionizing for the species. If a first fluid having a first concentration of the species is situated on a first side of the membrane and a second fluid having a second concentration of the species is situated on the opposite side of the membrane, and the first concentration differs from the second concentration, then an electrical signal, for example an electrical voltage proportional to a ratio of the concentrations, can be tapped off between the first side and the second side. The first concentration of the first fluid can be a concentration to be measured. The second concentration of the second fluid can be a reference concentration. The reference concentration can be provided, for example, by a fluid having a known, stable composition. In particular, the sensor can be an oxygen sensor. A catalyst, for example platinum, can then be arranged on both sides of the membrane, which is conductive for oxygen ions. The catalyst ionizes oxygen atoms which are in contact with the catalyst. In this case, a quantity of the ionized atoms is in equilibrium with the oxygen concentration in the fluid on the respective side of the membrane. At the catalyst, oxygen ions and electrons become free as a result of the ionization. The oxygen ions migrate from the side having the higher oxygen concentration to the side having the low concentration, in order to compensate for the concentration gradient. The membrane is electrically insulating and split-off electrons result in a positive voltage potential, while an excess of ions leads to a negative voltage potential. An electrical voltage between the voltage potentials forms an electrical signal. The membrane and alternatively or supplementarily the ionizing coating of the membrane can require a minimum temperature in order to function completely satisfactorily. For this purpose, one or more heating elements can be arranged on and alternatively or supplementarily around the membrane. The heating elements can have a high ohmic resistance and, in the event of a current flow through the heating elements, provide heat for regulating the temperature of the membrane.

A carrier material can be understood to be a plate, for example, into which conductor tracks and alternatively or supplementarily functional elements can be integrated. The conductor tracks and/or functional elements can also be arranged on a surface of the carrier material. A semiconductor substrate can be, for example, a monocrystalline or polycrystalline semiconductor material. The heating element can be electrically insulated from signal lines. The carrier material can be designed to form a chip. The heating element can be arranged around the sensor element in a meandering fashion, for example, in order to achieve a long usable length of the heating element. A microelectronic unit can have active and passive components, for example. The microelectronic unit can at least partly consist of doped semiconductor substrate.

In accordance with one exemplary embodiment, the microelectronic unit can have an interface to a sensor bus. The microelectronic unit can be designed to operate the heating element and the sensor element using electrical energy from the sensor bus. An interface can be a releasable and reconnectable connection to the sensor bus. The interface can be standardized. The interface can also be embodied as a soldering connection at which electrical conductors of the bus are connected to the microelectronic unit and/or the conductor tracks of the carrier material. In this way, no separate lines are required in order to supply the microelectronic unit and the heating element with energy. A sensor bus can be a data line via which a plurality of devices connected to the sensor bus can communicate by means of a standardized communication protocol. By way of example, the communication protocol can prescribe a form of bus signals which can be communicated on the sensor bus. The sensor bus can be controlled by a control unit. The sensor bus can have a plurality of cores. The control unit can provide a supply voltage via the sensor bus. A power output of the sensor bus can be limited by a performance of the control unit and alternatively or supplementarily by a conduction cross section of the cores of the sensor bus.

The sensor element, the heating element and the microelectronic unit can be integrated into the carrier material. As a result of an integration of all the constituent parts of the sensor in the carrier material, the sensor can be produced by means of semiconductor technology, as a result of which large numbers are possible in conjunction with low unit costs.

The sensor element and the heating element can be arranged on a first substrate. The microelectronic unit can be arranged on a second substrate. By virtue of the sensor being separated into two chips that can be produced independently of one another, the two chips can be manufactured in parallel, the finished chips being connected to one another by means of soldering connections, for example. By virtue of two separate chips, it is also possible to achieve a thermal decoupling of the microelectronic unit from the sensor element, as a result of which the sensor can be used at higher temperatures.

The carrier material can be embodied in a rod-shaped fashion. In the case of a rod-shaped carrier material, the sensor element with the heating element can be arranged at a first end of the carrier material, while the microelectronic unit is arranged at another end of the carrier material. There can be a largest possible distance between the sensor element and the microelectronic unit. As a result of the distance, the thermal loading of the microelectronic unit can be kept low, which can lead to an increased operating temperature of the sensor element. If the semiconductor material has a low thermal conductance, the carrier material can have a shorter length in order to achieve the same thermal loading for the same operating temperature. If the microelectronic unit is additionally manufactured from materials having higher temperature resistance, then the microelectronic unit can be arranged very near or directly alongside the sensor element, as a result of which the sensor overall can have very small dimensions.

The sensor element can be embodied as a thin-film membrane having electrodes on both sides, said electrodes being permeable for a species to be measured, wherein the sensor element is arranged between a measurement volume and a reference volume. The sensor can be produced using thin-film technology. By means of a thin-film membrane, a change in the concentration difference can be mapped particularly rapidly by the sensor in the sensor signal.

A method for operating a microelectrochemical sensor from a sensor bus comprises the following steps:
applying a heating voltage to a heating element of the sensor in order to regulate the temperature of a chemosensitive sensor element of the sensor, wherein the heating element is supplied with the heating voltage from the sensor bus via a microelectronic unit of the sensor;
detecting a sensor signal at the temperature-regulated sensor element by means of the microelectronic unit, wherein the sensor signal represents at least one concentration of a chemical species at the sensor element; and
determining a bus signal for provision on the sensor bus, wherein the bus signal is determined by the microelectronic unit using the sensor signal and electrical energy from the sensor bus.

A current flow through the heating element can be caused by the heating voltage. The heating voltage can be regulated by a microelectronic unit of the microelectrochemical sensor. The microelectronic unit can be supplied by the supply voltage of the sensor bus. By way of example, a temperature sensor can be arranged at the sensor element, wherein the microelectronic unit can regulate the heating voltage using a signal of the temperature sensor. The heating voltage can be fed from the supply voltage. By way of example, the heating voltage can be controlled by means of a pulse width modulation by the microelectronic unit. The microelectronic unit can also convert the sensor signal into a bus signal. By way of example, the bus signal can map a change in the sensor signal over a predetermined period of time. Alternatively or supplementarily, the bus signal can map a profile of the sensor signal during the predetermined period of time. The predetermined period of time can be defined, for example, by means of a clock signal on the sensor bus. The sensor element can also be supplied with an operating voltage by the microelectronic unit, which operating voltage can likewise be generated using the supply voltage of the sensor bus. By way of example, the operating voltage can enable different sensitivities of the sensor element and/or the operating voltage can be used for adjusting an operating point of the sensor element in order to react to different environmental conditions. The operating voltage can also be used for repelling the chemical species in order to put the sensor into an initial state with known conditions.

The bus signal can be amplified by a predetermined gain factor using the electrical energy from the sensor bus. The microelectronic unit can furthermore filter the sensor signal and/or the bus signal in order to improve a signal quality. The microelectronic unit can determine the bus signal using a sensor characteristic curve of the sensor element. The sensor characteristic curve can represent a relationship of the sensor voltage and the concentration. The microelectronic unit can compensate for a system-governed offset of the sensor signal in order to obtain a bus signal according to the requirements.

The bus signal can be digitized using the electrical energy. The sensor signal can be an analog signal. The microelectronic unit can carry out an analog/digital conversion in order to determine the bus signal. A digital signal can map the analog signal in a finite number of steps. The digital signal can readily be processed further.

The method can comprise a step of receiving at least one further sensor signal of a further sensor element. In this case, the bus signal can furthermore be determined using the at least one further sensor signal. The microelectronic unit can supply and alternatively or supplementarily control a plurality of sensor elements. The microelectronic unit can simultaneously evaluate the sensor signals of the different sensor elements. The microelectronic unit can likewise evaluate the sensor signals in a time-staggered manner. The microelectronic unit can also supply at least one further heating element with a further heating voltage. The sensor can have an interface to the at least one further sensor element if the at least one further sensor element is arranged remotely from the sensor.

The method can comprise a step of providing the bus signal on the sensor bus, wherein the bus signal is provided in response to a request signal on the sensor bus. A request signal can be transmitted by the control unit in order to be able to transfer the data via the sensor bus in a controlled manner. The request signal can be addressed to a plurality of receivers of the sensor bus. The request signal can also be addressed only for the sensor. The bus signal can then be provided in a reserved time window.

BRIEF DESCRIPTION OF THE DRAWINGS

The disclosure is explained in greater detail by way of example below with reference to the accompanying drawings, in which.

DETAILED DESCRIPTION

In the following description of preferred exemplary embodiments of the present disclosure, identical or similar reference signs are used for the elements that act similarly and are illustrated in the different figures, a repeated description of said elements being dispensed with.

Figure 1:
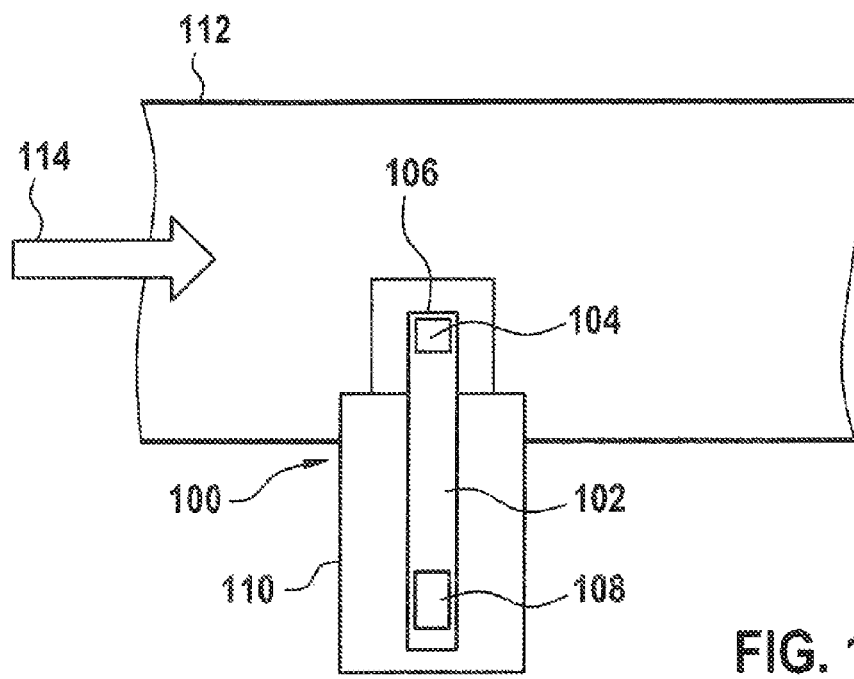
FIG. 1 shows a schematic illustration of a microelectrochemical sensor in accordance with one exemplary embodiment of the present disclosure.

FIG. 1 shows a block diagram of a microelectrochemical sensor 100 in accordance with one exemplary embodiment of the present disclosure. The sensor 100 comprises a carrier material 102, a chemosensitive sensor element 104, a heating element 106 and a microelectronic unit 108. The sensor 100 is arranged in a housing 110. The housing 110 is inserted into an exhaust gas duct 112, such that the sensor element 104 projects into the exhaust gas duct and the microelectronic unit 108 is arranged outside the exhaust gas duct 112. The carrier material 102 consists of a semiconductor substrate and is fashioned in a rod-shaped manner. In accordance with a further exemplary embodiment, instead of a semiconductor substrate, a substrate material is used which does not necessarily have semiconducting properties but can be processed and/or structured by means of semiconductor processes. Such a substrate material can be, for example, a photosensitive glass, such as Foturan. It is therefore also possible to use a substrate material which does not have semiconducting properties. The chemosensitive sensor element 104 is arranged in a first partial region of the carrier material 102. The first partial region is arranged at a first end of the rod-shaped carrier material 102. The heating element 106 is arranged in the region of the sensor element 104. The heating element 106 is designed to regulate the temperature of the sensor element 104. The microelectronic unit 108 is arranged in a second partial region of the carrier material 102. The second partial region is arranged at a second end of the rod-shaped carrier material 102. The microelectronic unit 108 has an interface to a sensor bus with a power-limited energy supply capacity. The microelectronic unit 108 is connected to the sensor element 104 and the heating element 106 via conductor tracks integrated into the carrier material 102. The microelectronic unit 108 is designed to operate the heating element 106 and the sensor element 104 using electrical energy from the sensor bus. The housing 110 encloses the sensor 100. The housing 110 is embodied such that the sensor element 104 at least with one side is in direct contact with an exhaust gas flow 114 which flows through the exhaust gas duct 112 during operation. Therefore, during operation the sensor element 104 is arranged in the exhaust gas 114 and thus in a hot measurement region. The rod-shaped Si carrier 102 results in a colder electronic unit 108. In this case, silicon is mentioned as material of the carrier 102 only by way of example. As already explained, a different substrate material can also be used.

In the case of the sensor 100 illustrated in FIG. 1, the sensor element 104 and the microelectronic unit 108 are manufactured on a silicon substrate 102, for example. This results in maximum operating temperatures of approximately 200° C. for the microelectronic unit 108. In this case, the sensor 100 is embodied as a small rod, the sensor element 104 being processed as a hot chip region on one side and the microelectronic unit 108 being processed on the opposite side.

The sensor element 104 and the microelectronic unit 108 can also firstly be manufactured on two individual chips 102. The two chips 102 are then connected in the form of a hybrid construction such that although they are electrically contact-connected to one another, they are thermally decoupled from one another to a sufficiently great extent.

The approach presented here can be used for example for a lambda probe 110 or further ceramic gas sensors, such as e.g. $NO_x$ sensors (nitrogen oxides), HC sensors (hydrocarbons), and/or $NH_3$ sensors (ammonia).

Figure 2:
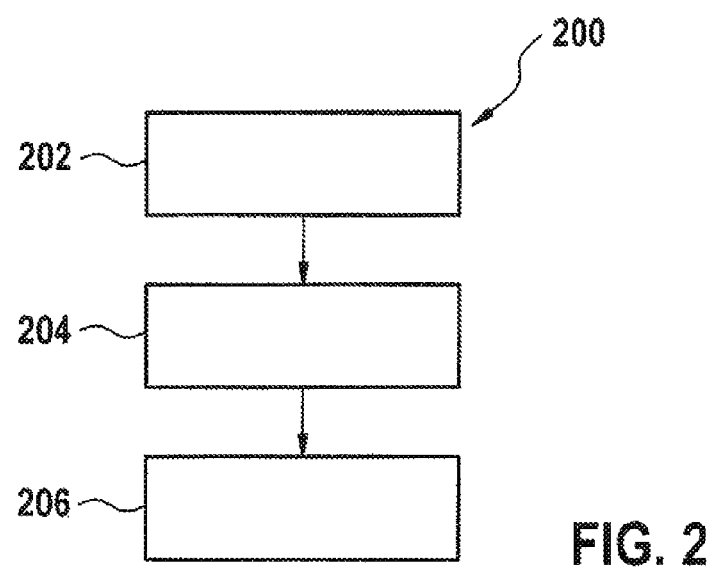
FIG. 2 shows a flow chart of a method for operating a microelectrochemical sensor from a sensor bus in accordance with one exemplary embodiment of the present disclosure.

FIG. 2 shows a flow chart of a method 200 for operating a microelectrochemical sensor from a sensor bus in accordance with one exemplary embodiment of the present disclosure. The method 200 can be performed on a sensor as described in FIG. 1. The method 200 comprises a step 202 of applying, a step 204 of detecting and a step 206 of determining. In step 202 of applying, a heating voltage is applied to a heating element of the sensor in order to regulate the temperature of a chemosensitive sensor element of the sensor. In this case, the heating element is supplied with the heating voltage from the sensor bus via a microelectronic unit of the sensor. In step 204 of detecting, a sensor signal at the temperature-regulated sensor element is detected by the microelectronic unit. The sensor signal represents at least one concentration of a chemical species at the sensor element. In step 206 of determining, a bus signal for provision on the sensor bus is determined. The bus signal is determined by the microelectronic unit using the sensor signal and electrical energy from the sensor bus.

Figure 3:
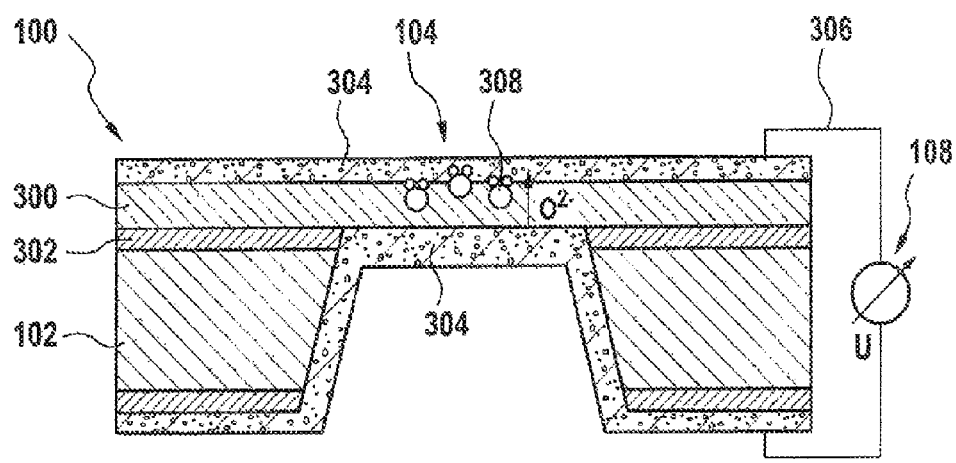
FIG. 3 shows a sectional illustration of a microelectrochemical sensor in accordance with one exemplary embodiment of the present disclosure.
Figure 4:
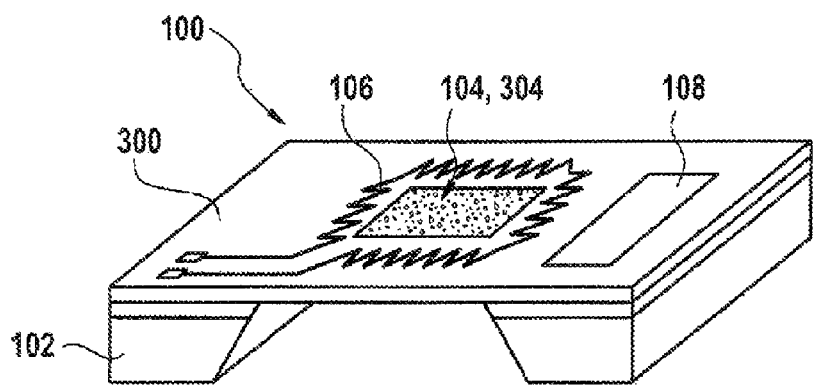
FIG. 4 shows a spatial illustration of a microelectrochemical sensor in accordance with one exemplary embodiment of the present disclosure.

On account of the small space requirement of the miniaturized electrochemical sensor presented here, as illustrated in FIGS. 1, 3 and 4, for example, the heating power requirement can be drastically reduced compared with conventional ceramic exhaust gas sensors. In this case, a lateral membrane size is, for example, 5 to 5000 square micrometers ($\mu m^2$), in particular, the membrane size can comprise an area of 10 to 400 square micrometers. This in turn makes it possible that the entire energy supply of the sensor, that is to say of the sensor element, of the microelectronic unit and of the heater, can be effected via the bus system. By way of example, in a PSI5 standard, a voltage of up to 11 volts and a current of up to 105 milliamperes (mA), that is to say a power of approximately 1 watt, are available. The power requirement of the sensor is predominantly determined by the heater of the sensor element. Heating powers of less than 1 watt, typically in the range of 10 to 500 milliwatts (mW), can be realized here, which can thus be provided directly via the PSI5 bus, for example.

By means of the integrated microelectronic unit, further functions can be realized directly on the sensor chip. By way of example, signal amplification can be effected directly on the sensor chip. Signal filtering can likewise be effected directly on the sensor chip. The signal of the sensor element can be digitized directly on the chip using an analog/digital conversion. By means of multiplexing, a plurality of different sensors or sensor elements can be driven or read. The microelectronic unit integrated in the chip can furthermore carry out a linearization of the lambda step-change characteristic curve. The microelectronic unit can likewise carry out an offset calibration of the sensor characteristic curve. The microelectronic unit can be designed to communicate with the sensor bus system.

FIG. 3 shows a sectional illustration of a microelectrochemical sensor 100 in accordance with one exemplary embodiment of the present disclosure. The sensor 100 corresponds to a sensor as described in FIG. 1. FIG. 3 illustrates the first partial region of the sensor 100. The second partial region with the microelectronic unit 108 is shown schematically here. The sensor 100 has a layered construction. During production, the carrier material 102 was structured by method steps of semiconductor technology and was provided with functional layers on both sides. The sensor element 104 consists of a ceramic layer 300, which is permeable to ions of at least one chemical species and was applied to one side of the carrier material 102 using at least one intermediate layer 302. The carrier material 102 and the intermediate layer 302 were removed in the region of the sensor element 104, such that the ceramic layer 300 is exposed on both sides. At least in the region of the sensor element 104, the ceramic layer 300 is fashioned as ionizing for the chemical species. In the exemplary embodiment illustrated, a catalyst 304 was applied to the ceramic layer 300 on both sides. The sensor 100 here is an oxygen sensor. Therefore, platinum was applied as the catalyst 304. The layers 304 composed of platinum are porous. Since platinum is electrically conductive, the catalyst 304 here performs a double function. The catalyst 304 is electrically conductively connected to the microelectronic unit 108 via conductor tracks 306. The conductor tracks 306 are illustrated schematically here, but are actually integrated into the carrier material 102, that is to say arranged on and/or in the carrier material 102. The heating element is concealed here by the layer of catalyst 304. The heating element is arranged in the region of the sensor element 104 and designed, by means of heat emission during a current flow through the heating element, to emit heat to the sensor element 104 in order to regulate the temperature of the sensor element 104. The heating element is likewise connected to the microelectronic unit 108 via conductor tracks for the supply of current.

If a higher concentration of the chemical species, here oxygen, is present on one side of the sensor element 104 than on the other side, oxygen ions 308 migrate through the ceramic layer 300 in order to balance the concentrations. Since the catalyst 304 ionizes the oxygen and at the same time conducts the electrons obtained in this case, a voltage gradient arises between the two sides since an excess of electrons arises on one side and a deficiency of electrons prevails on the other side. The voltage gradient is tapped off as sensor signal U by the microelectronic unit 108. The sensor signal can be designated as Nernst voltage $U_{Nernst}$. Since the sensor signal U is tapped off without current conduction, the microelectronic unit 108 uses electrical energy from the sensor bus to generate a bus signal representing the sensor signal U.

The miniaturized electrochemical sensor element 104 illustrated in FIG. 3 is realized using an ion-conducting thin-film membrane 300 arranged in a manner embedded into a semiconductor substrate 102. The manufacture of the sensor element 104 using semiconductor process technology makes it possible for the microelectronic unit 108 required for sensor signal conditioning at the same time to be integrated near the sensor element 104. However, the maximum permissible operating temperature of the microelectronic unit 108 constitutes a limitation for the operating temperature of this combination of sensor element 104 and microelectronic unit 108.

In the exemplary embodiment as a lambda probe 100 illustrated here, an exhaust gas guiding volume is arranged on a top side of the ceramic layer 300. The exhaust gas has a lower oxygen concentration than a reference air that is in contact with the ceramic layer 300 on an underside of the ceramic layer 300. Oxygen ions 308 migrate from the reference air to the exhaust gas since they are driven by a concentration gradient from the oxygen concentration in the reference air to the oxygen concentration in the exhaust gas.

FIG. 4 shows a spatial illustration of a microelectrochemical sensor 100 in accordance with one exemplary embodiment of the present disclosure. The sensor 100 corresponds to the sensor in FIG. 3. In addition to FIG. 3, the heating element 106 is illustrated here. The heating element 106 is embodied as a meander or zigzag conductor track around the sensor element 104. The heating element 106 is connected to the microelectronic unit 108 via conductor tracks embedded into the carrier material 102. Here, the sensor element 104 is embodied in a rectangular fashion and likewise connected to the microelectronic unit 108 via conductor tracks embedded into the carrier material 102. In contrast to FIG. 3, the catalyst 304 is applied to the ceramic layer 300 only in the region of the sensor element 104. By virtue of the limited area equipped with catalyst 304, a precise measurement result can be achieved. The carrier material 102 is composed of heat-resistant material and has a low thermal conductance. The ceramic layer 300 is likewise composed of heat-resistant material. The active and passive components of the microelectronic unit were produced from heat-resistant material. Therefore, the microelectronic unit 108 here is arranged at a small distance from the sensor element 104. In addition, the microelectronic unit 108 is embedded into the ceramic layer 300, as a result of which the microelectronic unit 108 is well protected. As a result of the small distance, the sensor 100 has very small dimensions. Overall, the sensor 100 can be operated at higher temperatures than, for example, the sensor 100 in FIG. 1.

In other words, FIG. 4 shows a microelectrochemical sensor 100 with integrated electronic unit 108. The sensor 100 was designed using insights from research activities for the miniaturization of the high temperature fuel cell (SOFC, solid oxide fuel cell). In order to produce the sensor 100, ceramic materials from conventional SOFC technology and microfabrication steps from semiconductor process technology were combined in order to create the microelectrochemical sensor.

A miniaturized ceramic exhaust gas sensor 100 in accordance with the approach presented here is shown. The lambda probe, in particular, is technologically very close to the SOFC. The base material for both applications is a ceramic 300 that conducts oxygen ions, said ceramic being embodied as usually yttrium-stabilized zirconium oxide, YSZ. Pt (platinum), for example, can be used as electrode material. The sensor 100 presented here is designed by means of a miniaturization approach using semiconductor process technology. The function of the lambda probe is realized by means of ion-conducting thin-film layers 300 on a substrate material 102 (chip) that can be manufactured by a semiconductor process.

The sensor element 104 and the microelectronic unit 108 are manufactured on a semiconductor substrate 102 having high temperature stability, such as e.g. SiC (silicon carbide) or GaN (gallium nitride). The integration of the electronic unit 108 having high temperature stability then makes it possible that the sensor element 104 and the microelectronic unit 108 can be realized directly on a chip 102 and in direct proximity to one another.

In this case, electrochemical sensor elements 104 manufactured by means of semiconductor process technology are arranged with a suitable microelectronic unit 108 in direct proximity to the sensor element 104. This can be implemented either directly on the sensor chip 102 or as a hybrid construction with a second chip 102.

As a result, the entire signal conditioning and linking to the sensor bus can take place directly on the sensor chip 102. The power consumption of the miniaturized electrochemical sensor 100 presented here, including the integrated microelectronic unit 108, is so low in this case that an electrical voltage of the sensor bus suffices as sensor operating voltage. Additional cost-intensive lines that are required in conventional lambda probes both for the heater voltage supply and for the coupling to an external sensor control unit are thus obviated. Furthermore, an external sensor control unit can be completely dispensed with, with the result that both costs and structural space can be saved.

The exemplary embodiments described and shown in the figures have been chosen merely by way of example. Different exemplary embodiments can be combined with one another completely or with regard to individual features. Moreover, one exemplary embodiment can be supplemented by features of a further exemplary embodiment. Furthermore, method steps according to the disclosure can be performed repeatedly and in a different order from that described.

What is claimed is:

1. A method of using a microelectrochemical sensor, comprising:
    supplying a heating voltage using a sensor bus;
    applying the heating voltage to a heating element via a microelectronic unit, wherein the heating element is configured to regulate a temperature of a chemosensitive sensor element including a thin-film membrane having a respective electrode on each side, the respective electrode permeable for a species to be measured;
    detecting a sensor signal at the chemosensitive sensor element using the microelectronic unit, wherein the sensor signal corresponds to at least one concentration of a chemical species at the chemosensitive sensor element; and
    determining a bus signal for provision on the sensor bus using the microelectronic unit, and based at least in part upon the sensor signal and electrical energy from the sensor bus.

2. The method of using a microelectrochemical sensor according to claim 1, wherein determining the bus signal includes amplifying the bus signal by a predetermined gain factor using the electrical energy.

3. The method of using a microelectrochemical sensor according to claim 1, wherein determining the bus signal includes digitizing the bus signal using the electrical energy.

4. The method of using a microelectrochemical sensor according to claim 1, further comprising receiving at least one further sensor signal of a further chemosensitive sensor element, wherein determining the bus signal is further based at least in part upon the at least one further sensor signal.

5. The method of using a microelectrochemical sensor according to claim 1, further comprising providing the bus signal on the sensor bus in response to a request signal on the sensor bus.

6. A microelectrochemical sensor comprising:
    a carrier material that includes:
        a semiconductor substrate; or
        a material defined by a semiconductor-process structure;
    a chemosensitive sensor element positioned in a first partial region of the carrier material;
    a heating element positioned in a region of the chemosensitive sensor element, and configured to regulate a temperate of the chemosensitive sensor element; and
    a microelectric unit positioned in a second partial region of the carrier material, wherein the microelectric unit:
        is connected to the chemosensitive sensor element and the heating element via conductor tracks integrated into the carrier material; and
        is configured to operate the heating element and the chemosensitive sensor element,
    wherein:
        the chemosensitive sensor element includes a thin-film membrane having a respective electrode on each side;
        the respective electrode is permeable for a species to be measured; and
        the chemosensitive sensor element is positioned between a measurement volume and a reference volume.

7. The microelectrochemical sensor according to claim 6, wherein the microelectric unit includes an interface to a sensor bus, and is configured to operate the heating element and the chemosensitive sensor element using electrical energy from the sensor bus.

8. The microelectrochemical sensor according to claim 6, wherein the chemosensitive sensor element, the heating element, and the microelectric unit are integrated into the carrier material.

9. The microelectrochemical sensor according to claim 6, wherein:
    the chemosensitive sensor element and the heating element are positioned on a first substrate; and
    the microelectric unit is arranged on a second substrate.

10. The microelectrochemical sensor according to claim 6, wherein the carrier material is defined by a rod shape.

* * * * *